United States Patent [19]

Kunz et al.

[11] 4,371,545
[45] Feb. 1, 1983

[54] ISOPROPYL AMINE COMPOUNDS

[75] Inventors: Wilhelm Kunz, Wachtberg-Villiprott; Klaus Gruber, Bonn, both of Fed. Rep. of Germany

[73] Assignee: Dolorgiet Beteiligungs GmbH, Fed. Rep. of Germany

[21] Appl. No.: 244,823

[22] Filed: Mar. 17, 1981

Related U.S. Application Data

[63] Continuation-in-part of Ser. No. 73,369, Sep. 7, 1979, abandoned.

[30] Foreign Application Priority Data

Sep. 11, 1978 [DE] Fed. Rep. of Germany ....... 2839475

[51] Int. Cl.$^3$ .................. C07C 93/02; A61K 31/135
[52] U.S. Cl. ............................. 424/330; 564/350
[58] Field of Search ...................... 564/350; 424/330

[56] References Cited

U.S. PATENT DOCUMENTS

| 3,275,629 | 9/1966 | Baizer | 564/350 |
| 3,331,850 | 7/1967 | Youngdale | 564/350 |
| 3,501,769 | 3/1970 | Crowther | 564/350 |
| 3,542,872 | 11/1970 | Koppe | 564/350 |
| 3,742,023 | 6/1973 | Koppe | 564/350 |
| 3,872,147 | 3/1975 | Koppe | 564/350 |
| 4,085,136 | 4/1978 | Tucker | 564/350 |

Primary Examiner—Michael L. Shippen
Attorney, Agent, or Firm—Birch, Stewart, Kolasch and Birch

[57] ABSTRACT

The present invention relates to new isopropyl amine compounds and processes for preparing the same. This invention also relates to pharmaceutical compositions containing said isopropyl amine compounds.

The new isopropyl amine compounds correspond to the following general formula:

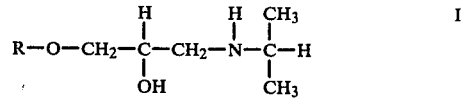

wherein R represents a nitrophenyl radical, which may be substituted one or more times by halogen, preferably chloride, and/or by lower straignt- or branched-chain alkyl radicals containing from 1 to 4 carbon atoms an/or by alkoxy radicals containing from 1 to 3 carbon atoms and salts thereof with physiologically compatible acids.

3 Claims, No Drawings

ISOPROPYL AMINE COMPOUNDS

CROSS REFERENCE TO RELATED APPLICATION

This application is a continuation-in-part of U.S. Ser. No. 73,369 filed on Sept. 7, 1979, now abandoned.

SUMMARY OF THE INVENTION

The present invention relates to new isopropyl amine compounds corresponding to the following general formula:

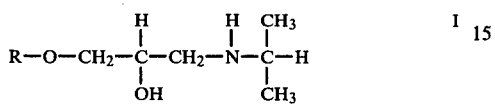

wherein R represents a nitrophenyl radical which may be substituted one or more times by halogen, preferably chlorine, and/or lower straight- or branched-chain alkyl radicals containing from 1 to 4 carbon atoms and-/or alkoxyl radicals containing from 1 to 3 carbon atoms: and to the salts thereof with physiologically compatible acids; to processes for the preparation of these new isopropylamine compounds and to the pharmaceutical application thereof by use of a pharmaceutical preparation including a compound according to the present invention and a pharmaceutically acceptable carrier or diluent.

The compounds according to the present invention corresponding to formula I above may be obtained by known methods, R in the following formulas having the same meaning as in formula I. For Example, the compounds of the present invention may be prepared:

(1) By reacting isopropylamine with an aryl glycidol ether corresponding to the following general formula:

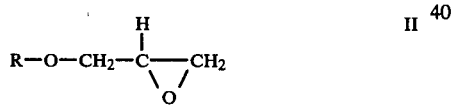

at an elevated temperature between about 20° and 60° C., optionally in the presence of an inert solvent such as methanol or water, or with a compound corresponding to the following general formula:

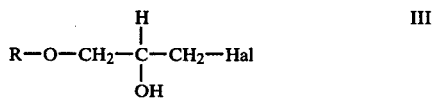

wherein Hal represents chlorine, bromine or iodine, at elevated temperature, optionally in the presence of an inert solvent and/or an acid acceptor.

(2) By reaction isopropylamino-2,3-oxidopropane or isopropylamino-2-hydroxypropane-3-halide with a phenol corresponding to the following general formula:

R—OH   IV at an elevated temperature between about 30° and 80° C., optionally in the presence of an inert solvent such as ethanol and/or in an alkaline medium such as aqueous solutions of sodium or potassium hydroxide.

(3) By reacting a compound corresponding to the following general formula:

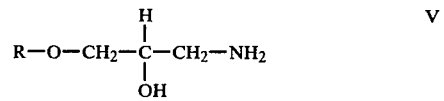

with an isopropyl halide, preferably isopropyl chloride, at an elevated temperature between about 30° and 80° C., optionally in the presence of an inert solvent such as isopropanole and/or an acid acceptor such as ammonia.

(4) By reducing a compound corresponding to the following general formula:

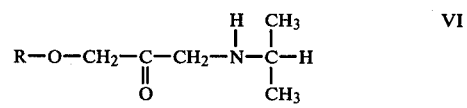

to the corresponding alcohol, for example by hydrogenation in the presence of suitable catalyst, such as platinum oxide, optionally in the presence of an inert solvent such as methanol.

(5) By hydrolyzing oxazolidones corresponding to the following general formula:

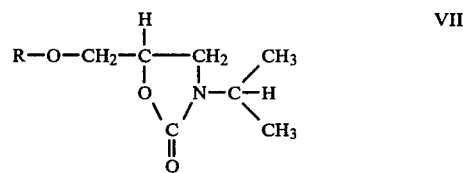

for instance by potassium or sodium hydroxide in aqueous solution.

From the bases, it is possible to prepare salts with physiologically compatible inorganic or organic acids.

Examples of physiologically acceptable inorganic and organic acids suitable for salt formation are hydrogen chloride, hydrogen bromide, hydrogen iodine, sulphuric acid, nitric acid, phosphoric acid, acetic acid, gluconic acid, lactic acid, malonic acid, maleic acid, succinic acid, fumaric acid, tartaric acid, citric acid, benzoic acid, $\beta$-oxy-naphtholic acid, embonic acid or theophylline acetic acid. The preferred salts are the hydrochlorides.

The physiologically acceptable salts are prepared by reacting the base in an alcoholic solution with the corresponding acid.

Pharmaceutical preparations are prepared by mixing the above compounds with a pharmaceutically acceptable carrier or diluent. The pharmaceutical preparations which are prepared by known methods may be in the form of pills, drages, tablets, solutions and the like. Useful solvents for preparing solutions of the above compounds include isotonic salt solutions.

The $\beta$-adrenergic blocking activity of the compound 1-(5-methyl-2-nitrophenoxy)-2-hydroxy-3-isopropylaminopropane-hydrochloride has been demonstrated in mammals such as mice, rats and cats. It is also to be expected that the above compound will have similar effects when administered to humans.

The above compound may be administered intravenously (I.V.) in an amount of between about 0.1 and 5 mg/kg of body weight. Similar doses would be expected for humans.

In accordance with the asymmetric center on the carbon atom on the 2-position of the side chain, the compounds according to the invention occur in the form of optically active isomers which may be separated by known methods such as the formation of salts with p-toluene tartaric acid and fractional crystallisation.

The isopropyl-amine derivatives according to the invention and the physiologically acceptable salts thereof show high β-adrenergic blocking activity and are capable of inhibiting or preventing platelet aggregation.

EXAMPLE 1

1-(5-methyl-2-nitrophenoxy)-2-hydroxy-3-isopropylaminopropane-hydrochloride 10.5 g of 1-(5-methyl-2-nitrophenoxy)-2,3-epoxypropane are heated under reflux for about 8 hours with 5 g of isopropylamine in 100 ml of ethanol. After the alcohol has been distilled off in vacuo, the residue is dissolved in benzene. This benzene solution is then saturated with hydrogen chloride while cooling with ice. The deposit is filtered off under suction, washed with acetone and recrystallized from isopropanol.

| m.p. 163–164° C. | |
|---|---|
| Analysis: $C_{13}H_{20}N_2O_4 \times HCl$ | |
| Molecular weight: 304.781 | |
| calculated: | found: |
| C 51,23% | 51,28% |
| H 6,95% | 7,03% |
| N 9,19% | 9,09% |

EXAMPLE 2

As an example of a pharmaceutical composition according to the invention, tablets are prepared as follows:

| Active ingredient | 40 mg | (400 g) |
|---|---|---|
| Maize starch | 89.4 mg | (894 g) |
| Dicalcium phosphate .2H$_2$O | 130.0 mg | (1300 g) |
| Silicic acid (Aerosil 300) | 0.1 mg | (1 g) |
| Magnesium stearate | 0.5 mg | (5 g) |
| Weight | 260.0 mg | (2.6 kg) |

The drug is mixed with the silicic acid and the mixture is finely ground (99%>50 μm). The resulting mixture is homogeneously mixed with the other components and the product is sieved.

By compressing the obtained composition using a suitable machine, tablets with a diameter of 9 mm and a weight of 260 mg are obtained.

TOXICITY

The acute toxicity of the inventive compound is determined by the method of Litchfield and Wilcoxon (J. Pharmacol. exp. Therap., 96 (1949), 99).

The following LD$_{50}$ values are determined:

Mouse

-continued

| p.o. ♀ ♂ | 1275 (1063–1530) mg/kg | in each case 10 ♀ and ♂ mice |
|---|---|---|
| i.p. ♀ ♂ | 250 (231–270) mg/kg | |
| i.v. ♀ ♂ | 105.0 (96.4–114.4) mg/kg | |

Rat

| p.o. ♀ ♂ | 1125 (802–1579) |
|---|---|
| i.p. ♀ ♂ | 192 (184–200) |
| i.v. ♀ | 68.9 (61.4–75.3) |
| ♂ | 80.0 (74.5–85.9) |

ANIMAL TESTS

A comparative screening test was conducted on anaestetized cats suffering from isoprenalin-induced tachycardia.

1. Object of the experiments

To provide an informative determination of the ED$_{50}$ of the test preparation on isoprenalin-induced tachycardia of anaesthetized cats as well as qualitative determination of the characteristic effect of the preparation on blood pressure and heart beat frequency in resting position.

2. Summary

Compared to propranolol, the compound of the invention proved to have good beta-blocking activity in the tests on isoprenalin-induced tachycardia of anaesthetized cats. Based on the ED$_{50}$ of propranolol (=1), the following efficiency was determined for the compound of the invention:

Propranolol—1

Compound of the invention—2.3

The compound of the invention effectively reduced the frequency of heart beat in resting position, the respective results depending on the original position and the dose administered.

An isoprenalin-induced drop in arterial blood pressure was reliably reduced and blocked, respectively, by the compound of the invention as well as by propranolol.

3. Test report

| 3.1 | Test preparation | compound of the invention |
|---|---|---|
| 3.1.1 | Reference preparation: | propranolol - HCL (Dociton$^R$, ampoules 1 mg, supplied by ICI-Pharma Arzneimittelwerk, Plankstadt). |
| 3.1.1.1 | Administered as: | aqueous solution in acqua ad injectabilia (Ampuwa). |
| 3.2 | Test animals: | male and female cats, weighing 1.6 to 3.2 kg, unfed Before start of the tests, the cats received no food for a period of 18 to 24 hours, water remaining available. |
| 3.3 | Test methods employed: | |
| 3.3.1 | Test conditions Anaesthetic: | hexobarbital (Evipan-Na), 90 mg/kg i.p. |
| | Respiration: | spontaneous after tracheotomy |
| | Preparatory measures: | catheterization of V. femoralis for injection of the test preparations; catheterization of A. femoralis for measuring arterial blood pressure; blood coagu- |

| | | -continued |
|---|---|---|
| | Variables measured: | lation suppressed with sodium heparinate, 600 units /kg i.v. phase and mean blood pressure, using a Statham pressure gauge and an HSE electromanometer; heart frequency by means of the pulse wave interval, using an HSE-EKA sphygmograph or HSE frequency couplers. |
| | Recording device: | Watanabe high-speec recorder |
| 3.3.2 | Administration of the test preparations: | |
| | Isoprenalin: | i.v. injection; dose 0.3 to 1 μg/kg; volume administered: 0.1 ml/kg; intervals between injections; 10 min. |
| | Test preparations: | i.v. injections, each 4 min. prior to the next isoprenalin injection; dosage range: 10 to 100 μg/kg and, respect., 100 to 1000 μg/kg; interval between injections: $\sqrt[2]{10}$; injection time: 10 sec. |
| 3.3.3 | Criteria determining the efficiency: | percentage reduction in isoprenalin-induced tachycardia; measured at maximum efficiency (4 min. after injection). |
| 3.3.4 | Analysis of the records obtained: | $ED_{50}$ is determined by graphic extrapolation on the curves showing the effectiveness of the dose administered. $ED_{50}$ means the dose (μg/kg i.v.) required for reducing tachycardia by 50% as compared to the original value. |

4. Results

Table 1 informs on the results of the above experiments. The quantitative criteria in this table are: reduction of isoprenalin-induced tachycardia in percent; $ED_{50}$ determined by graphic extrapolation on the curve showing the effectiveness of the respective dose; and relative activity which may be calculated as quotient from the $ED_{50}$ (μg/kg) of propranolol and the $ED_{50}$ of the test preparation.

The remaining data in the table refer to the characteristic effect of the test preparation on the heart beat frequency in resting position, arterial blood pressure in resting position, and reduction of isoprenalin-induced drop in blood pressure; the respective data are more of qualitative nature.

TABLE 1

Inhibition in isoprenalin-induced tachycardia achieved with the compound of the invention and with propranolol (quantitative results) as well as effect on the mean, isoprenalin-induced drop in arterial pressure, the mean arterial blood pressure and the heart beat frequency in resting position (qualitative results).

| Preparation | n | Dose (ug/kg) | Reduction in Tachycardia % (x + Sx) | $ED_{50}$ (ug/kg) | Rel. Activity | HR norm | m BP Isopr. | m BP norm |
|---|---|---|---|---|---|---|---|---|
| Propranolol | 6 | 10 | 18.4 ∓ 4.57 | 48 | =1 | + − +++ | + − +++R d.d. | + − ++ d.d. |
| | | 32 | 37.4 ∓ 4.07 | | | | | |
| | | 100 | 68.0 ∓ 4.61 | | | d.d. | | |
| Compound of the invention | 3 | 10 | 31.4 ∓ 5.6 | | | | | |
| | | 32 | 66.3 ∓ 5.48 | 21 | 2.3 | + − +++ d.d. | + − +++R d.d. | — |
| | | 100 | 80.2 ∓ 2.82 | | | | | |

HR norm = bradycardial effect (heart beat frequency in resting position).
m BP Isopr. = reduction in mean, isoprenalin-induced drop in arterial blood pressure.
m BP norm = effectiveness in lowering blood pressure (mean arterial pressure in resting position).
d.d. = dosage dependant.
R = reversal of blood pressure after isoprenalin injection.

What is claimed:

1. The compound 1-(5-methyl-2-nitrophenoxy)-2-hydroxy-3-isopropylaminopropane or a physiologically acceptable salt thereof.

2. A pharmaceutical preparation comprising the compound according to claim 1 or a physiological salt thereof and a pharmaceutically acceptable carrier or diluent.

3. A method for blocking β-adrenergic blocking activity in mammals comprising administering to said mammal an effective β-adrenergic blocking amount of the pharmaceutical preparation according to claim 2.

* * * * *